(12) United States Patent
Trebes et al.

(10) Patent No.: US 6,353,658 B1
(45) Date of Patent: Mar. 5, 2002

(54) MINIATURE X-RAY SOURCE

(75) Inventors: James E. Trebes; Gary F. Stone, both of Livermore; Perry M. Bell, Tracy; Ronald B. Robinson, Modesto, all of CA (US); Victor I. Chornenky, Minnetonka, MN (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/391,578

(22) Filed: Sep. 8, 1999

(51) Int. Cl.[7] .................................................. H01J 35/20
(52) U.S. Cl. .......................... 378/123; 378/121; 378/119
(58) Field of Search ................................ 378/119, 121, 378/122, 123, 136, 143, 65; 313/552, 559, 545

(56) References Cited

U.S. PATENT DOCUMENTS

| | | |
|---|---|---|
| 1,881,448 A | 10/1932 | Forde et al. |
| 3,508,059 A | 4/1970 | Vanderpool |
| 3,714,486 A | 1/1973 | McCrary |
| 3,752,990 A | 8/1973 | Fischer |
| 3,878,394 A | 4/1975 | Golden |
| 3,883,760 A | 5/1975 | Cunningham, Jr. |
| 3,920,999 A | 11/1975 | Drexler et al. |
| 3,970,884 A | 7/1976 | Golden |
| 4,060,731 A | 11/1977 | Rissi |
| 4,097,759 A | 6/1978 | Furbee et al. |
| 4,104,526 A | 8/1978 | Albert |
| 4,104,530 A | 8/1978 | Weiss |
| 4,104,531 A | 8/1978 | Weiss |
| 4,104,532 A | 8/1978 | Weiss |
| 4,109,154 A | 8/1978 | Taumann |
| 4,117,334 A | 9/1978 | Strauts |
| 4,143,275 A | 3/1979 | Mallozzi et al. |
| 4,163,901 A | 8/1979 | Azam et al. |

(List continued on next page.)

FOREIGN PATENT DOCUMENTS

| | | |
|---|---|---|
| DE | 2054738 | 5/1972 |
| DE | 26 08 418 A1 | 9/1977 |
| EP | 0 697 712 A1 | 2/1996 |
| EP | 0 860 180 A2 | 8/1998 |
| FR | 2 672 734 | 8/1992 |
| GB | 230183 | 3/1925 |
| JP | 0145098 | 8/1983 |
| WO | WO 97/07740 | 3/1997 |
| WO | WO 98/36796 | 8/1998 |
| WO | WO 98/48899 | 11/1998 |

OTHER PUBLICATIONS

Chornenky, V., "Intravascular Soft X–Ray Therapy", *Vascular Brachytherapy, Second Edition,* Chapter 48, pp. 561–567 (©1999).

(List continued on next page.)

*Primary Examiner*—Robert H. Kim
*Assistant Examiner*—Hoon K. Song
(74) *Attorney, Agent, or Firm*—L. E. Carnahan; Alan H. Thompson

(57) ABSTRACT

A miniature x-ray source capable of producing broad spectrum x-ray emission over a wide range of x-ray energies. The miniature x-ray source comprises a compact vacuum tube assembly containing a cathode, an anode, a high voltage feedthru for delivering high voltage to the anode, a getter for maintaining high vacuum, a connection for an initial vacuum pump down and crimp-off, and a high voltage connection for attaching a compact high voltage cable to the high voltage feedthru. At least a portion of the vacuum tube wall is highly x-ray transparent and made, for example, from boron nitride. The compact size and potential for remote operation allows the x-ray source, for example, to be placed adjacent to a material sample undergoing analysis or in proximity to the region to be treated for medical applications.

28 Claims, 4 Drawing Sheets

U.S. PATENT DOCUMENTS

| | | | |
|---|---|---|---|
| 4,359,660 A | 11/1982 | Smith et al. | |
| 4,368,538 A | 1/1983 | McCorkle | |
| 4,563,769 A | 1/1986 | Madsen | |
| 4,607,380 A | 8/1986 | Oliver | |
| 4,625,324 A | 11/1986 | Blaskis et al. | |
| 4,646,338 A | 2/1987 | Skillicorn | |
| 4,670,894 A | 6/1987 | Birnbach et al. | |
| 4,694,480 A | 9/1987 | Skillicorn | |
| 4,701,941 A | 10/1987 | Szirmai et al. | |
| 4,702,228 A | 10/1987 | Russell, Jr. et al. | |
| 4,715,054 A | 12/1987 | Kato et al. | |
| 4,789,997 A | 12/1988 | Madsen et al. | |
| 4,800,581 A | 1/1989 | Kujirai et al. | |
| 4,856,036 A | 8/1989 | Malcolm et al. | |
| 4,913,142 A | 4/1990 | Kittrell et al. | |
| 4,924,485 A | 5/1990 | Hoeberling | |
| 4,979,199 A | 12/1990 | Cueman et al. | |
| 5,077,771 A | 12/1991 | Skillicorn et al. | |
| 5,090,043 A * | 2/1992 | Parker et al. | 378/121 |
| 5,106,360 A | 4/1992 | Ishiwara et al. | |
| 5,111,493 A | 5/1992 | Siedband | |
| 5,148,463 A | 9/1992 | Woodruff et al. | |
| 5,153,900 A | 10/1992 | Nomikos et al. | |
| 5,165,093 A | 11/1992 | Miller et al. | |
| 5,199,939 A | 4/1993 | Dake et al. | |
| RE34,421 E | 10/1993 | Parker et al. | 378/121 |
| 5,264,801 A | 11/1993 | DeCou, Jr. et al. | |
| 5,369,679 A | 11/1994 | Sliski et al. | |
| 5,402,790 A | 4/1995 | Jang et al. | |
| 5,422,926 A | 6/1995 | Smith et al. | |
| 5,428,658 A | 6/1995 | Oettinger et al. | |
| 5,437,277 A | 8/1995 | Dumoulin et al. | |
| 5,442,678 A | 8/1995 | Dinsmore et al. | |
| 5,444,254 A | 8/1995 | Thomson | |
| 5,452,720 A | 9/1995 | Smith et al. | |
| 5,469,490 A | 11/1995 | Golden et al. | |
| 5,504,799 A | 4/1996 | Suzuki | |
| 5,509,045 A | 4/1996 | Kautz | |
| 5,511,107 A | 4/1996 | Sliski | |
| 5,528,652 A | 6/1996 | Smith et al. | |
| 5,566,221 A | 10/1996 | Smith et al. | |
| 5,621,780 A | 4/1997 | Smith et al. | |
| 5,623,139 A | 4/1997 | Sliski | |
| 5,627,871 A | 5/1997 | Wang | |
| 5,635,709 A | 6/1997 | Sliski et al. | |
| 5,729,583 A * | 3/1998 | Tang et al. | 378/122 |
| 5,748,699 A | 5/1998 | Smith | |
| 5,854,822 A | 12/1998 | Chornenky et al. | |

OTHER PUBLICATIONS

*Handbook of Vascular Brachytherapy,* Editors: Ron Waksman and Patrick W. Serruys, Publisher: Martin Dunitz, Ltd., pp. 103–105 (1998).

Wiedermann, J. et al., "Effects of high–dose intracoronary irradiaton on vasomotor function and smooth muscle histopathology", *American Physiological Society,* pp. H125–H132 (©1994).

* cited by examiner

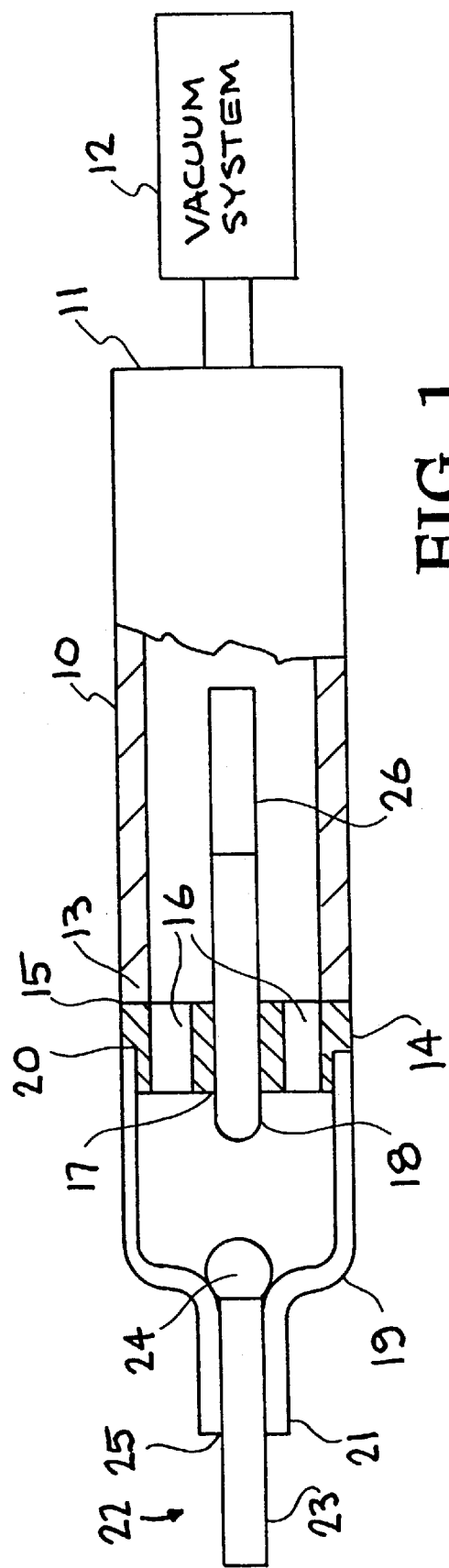
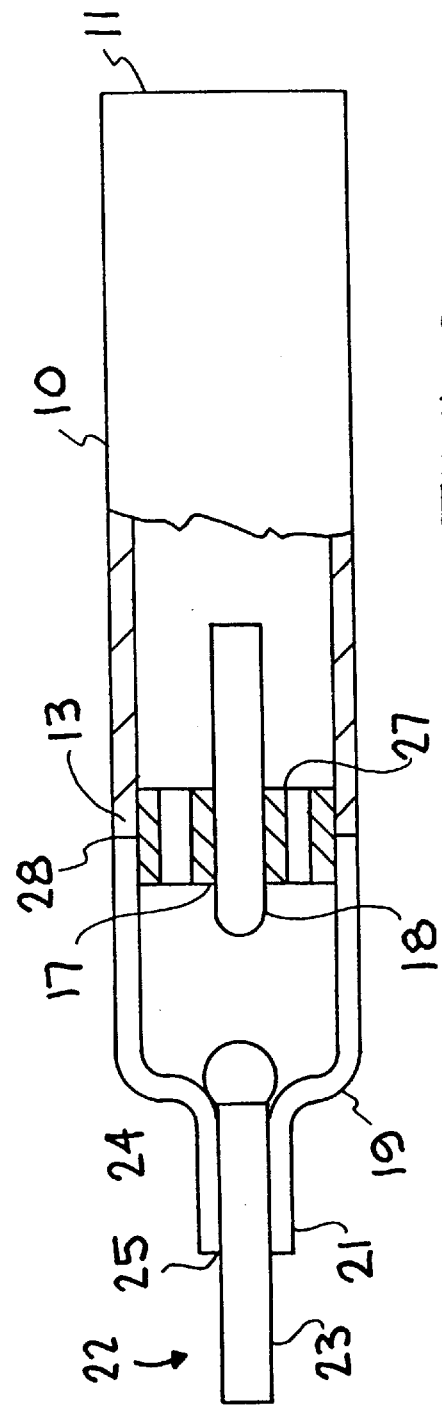
FIG. 1
FIG. 2

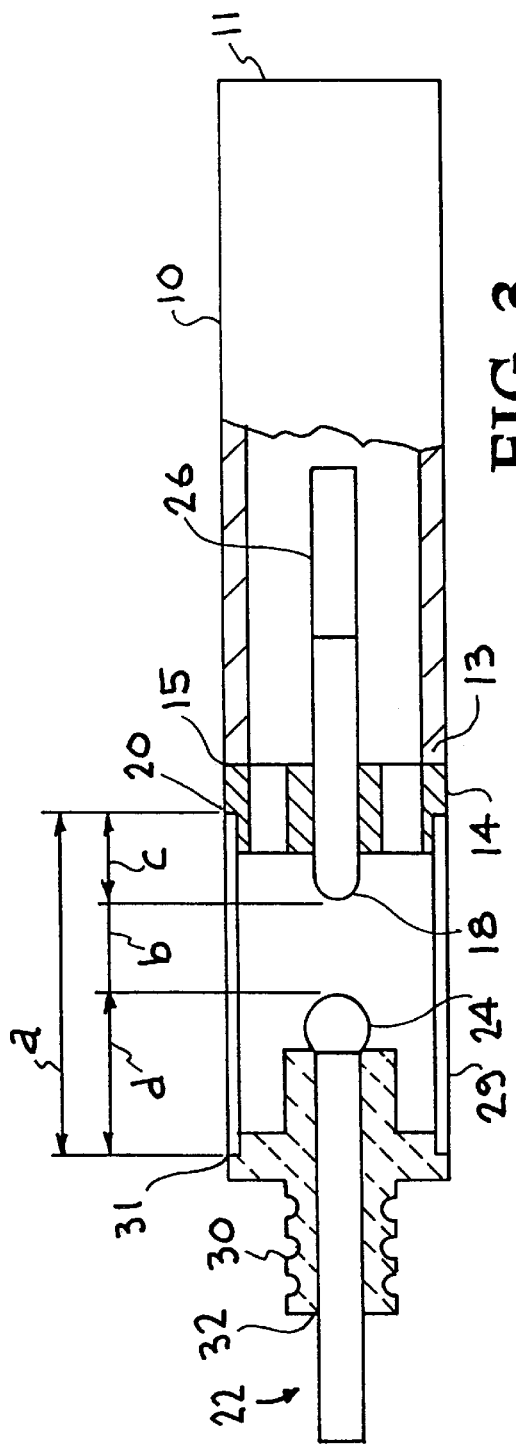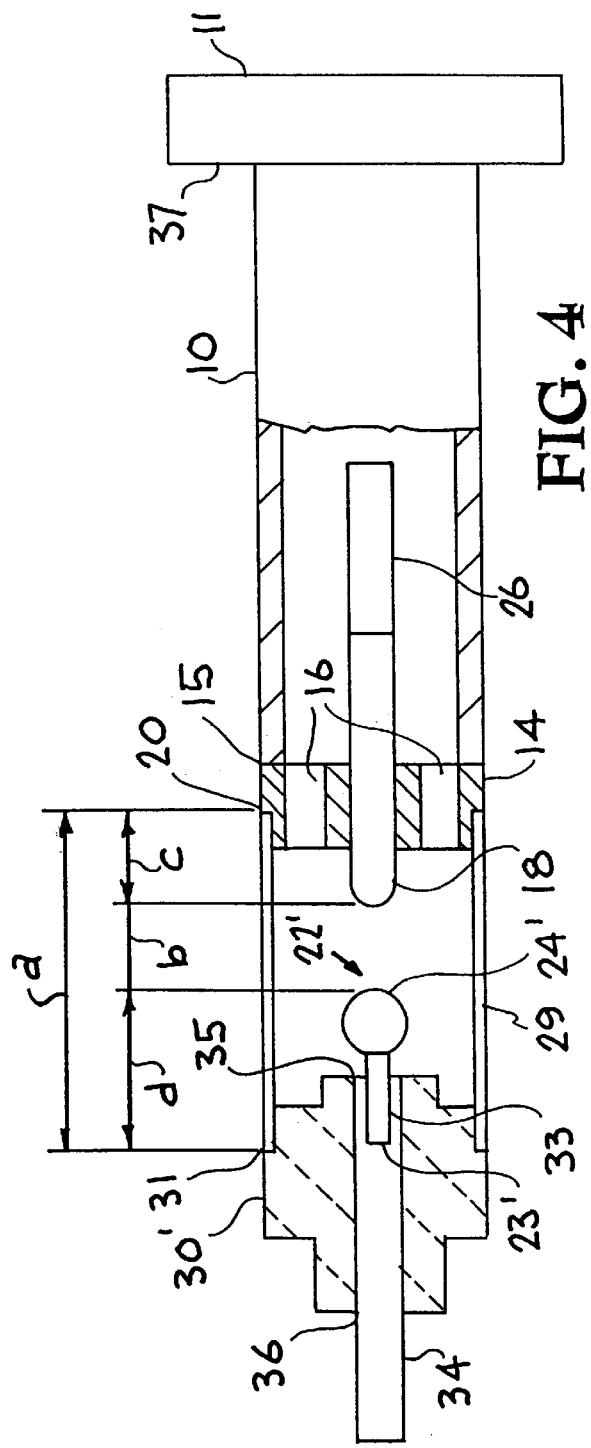

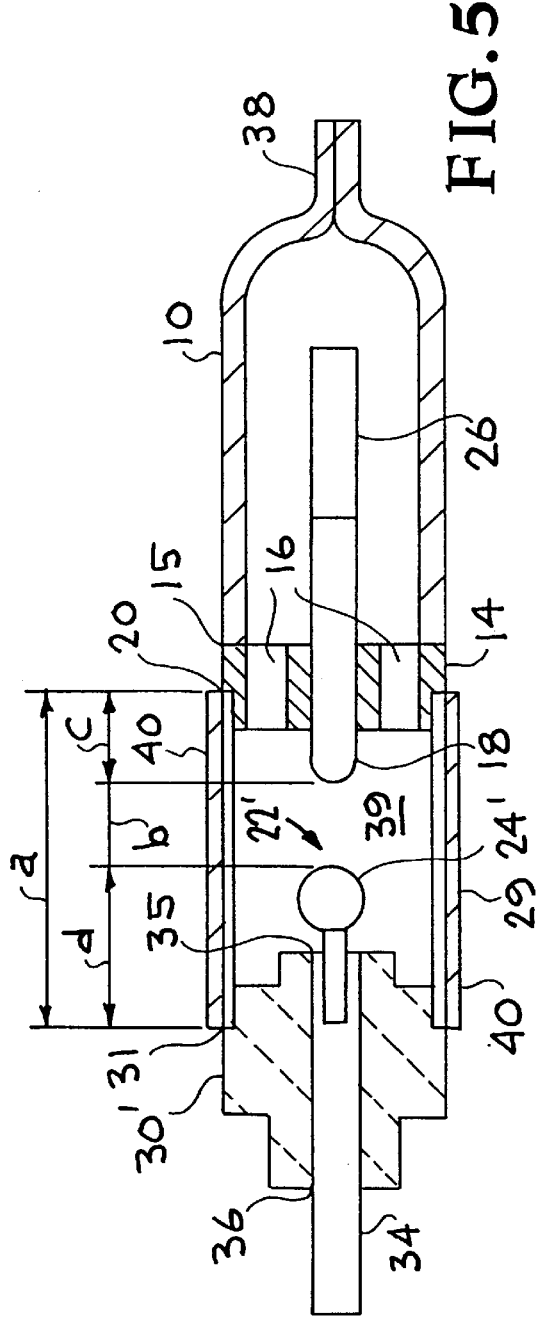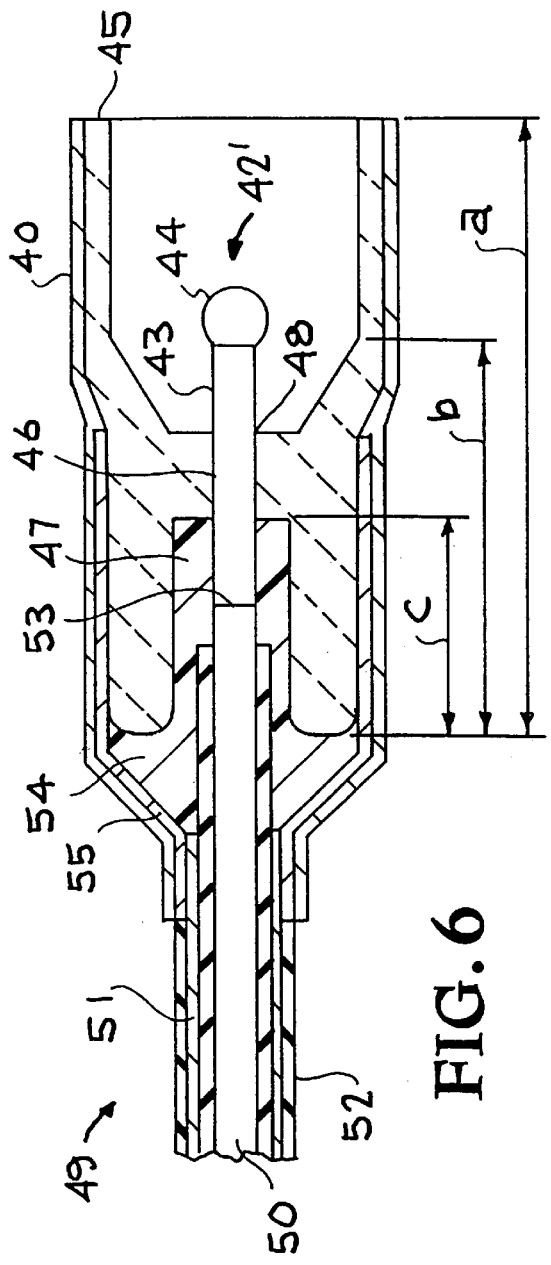

MINIATURE X-RAY SOURCE

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to x-ray sources, particularly to compact x-ray sources, and more particularly to a miniature x-ray source having millimeter scale size and capable of producing broad spectrum x-ray emission over a wide range of x-ray energies.

X-rays are typically produced in an assembly consisting of a vacuum housing, a high voltage feedthru, a high voltage connection to the feedthru, an anode, and a cathode. The assembly operates by applying a high voltage across a gap between the anode and the cathode. Electrons are emitted by the cathode and accelerated by the high voltage to the anode. The electrons impact on the anode and create both broadband and line radiation through collisional excitation of the atoms within the anode. The x-rays are emitted from the anode and propagate through the vacuum housing to be used for any given application. The vacuum housing must be highly transparent to the x-rays or have a high transparent window mounted in it to allow the x-rays to escape for use. The entire assembly is under vacuum to allow for efficient transport of the electrons from the cathode to the anode and to prevent a gas discharge or an electrical arc from forming, which would significantly reduce the voltage across the gap (reducing the x-ray energy) or destroying the assembly. Efficient production of x-rays and the production of x-rays with sufficient energy (5–40 keV or higher) for a wide range of applications requires the use of high voltages (5–40 kV or higher). The fabrication of compact x-ray sources has not been readily attainable due to the need to have high voltage over extremely small dimensions (~1 mm), high vacuum in extremely small volumes (cubic mms), and a high voltage connection of extremely small size (~1 mm).

Recently, an x-ray "catheter" was designed which comprises a flexible catheter shaft having an x-ray unit coupled to the distal end thereof. Such an approach is described in Application PCT/US96/3629 filed Aug. 22, 1996 (International Publication No. WO 97/07740 dated Mar. 6, 1997).

The present invention provides a solution to this need by the use of a miniature x-ray source having high voltage over small dimensions, high vacuum in small volumes, and a high voltage connection of small size. The miniature x-ray source of this invention comprises an anode having a curved end, a cathode, a high voltage feedthru, a highly x-ray transparent vacuum housing, a high voltage connection to a high voltage cable, a pump-through member with vacuum pump-out channels that holds the cathode, and a crimp-off or vacuum tube containing a getter. The various components are interconnected by brazing or welding techniques.

SUMMARY OF THE INVENTION

It is an object of the present invention to provide a miniature x-ray source.

A further object of the invention is to provide an x-ray source of millimeter scale size.

A further object of the invention is to provide a miniature x-ray source capable of producing broad spectrum x-ray emission over a wide range of x-ray energies.

Another object of the invention is to provide a miniature x-ray source for remote operations wherein the source can be placed adjacent to a point of use, which improves the signal level and allows for local measurements in confined or remote locations. In addition, the x-ray source is capable of using high voltages without causing adverse effects at the point of use.

Another object of the invention is to provide a miniature x-ray source which includes a transparent vacuum tube containing a cathode, an anode, a high voltage feedthru, a getter, a pump-through member for initial vacuum pump down and crimp-off, and a high voltage connection for attaching a cable to the feedthru.

Another object of the invention is to provide a miniature x-ray source, including a highly x-ray transparent vacuum tube assembly constructed, for example, from boron nitride.

Another object of the invention is to provide a miniature x-ray source using either a cold (field emission) or a hot filament cathode.

Other objects and advantages of the present invention will become apparent from the following description and accompanying drawings. The present invention is an x-ray source capable of producing broad spectrum x-ray emission over a wide range of x-ray energies. The miniature x-ray source has a wide range of applications, such as the treatment of arterial restenosis, cancer tumors, and for material analysis, since the source can be inserted into extremely confined spaces, such as inside the human body, inside an artery, or in close proximity to material to be x-ray analyzed. The x-ray source consists of an anode having a curved configuration, such as a tungsten ball on the end of a tungsten shaft; a cathode, such as a diamond-coated tungsten substrate or graphite; a high voltage feedthru made of material such as ceramic or Maycor; a highly x-ray transparent vacuum housing made from material, such as pyrolytic boron nitride (PBN); a high voltage connection to a high voltage cable, such as a coaxial cable, a pump-through member or cathode mount with vacuum pump-out channels, and a vacuum tube for crimp-off containing a getter.

BRIEF DESCRIPTION OF THE DRAWINGS

The accompanying drawings, which are incorporated into and form a part of the disclosure, illustrate embodiments of the invention and, together with the description, serve to explain the principles of the invention.

FIG. 1 is a cross-sectional view of an embodiment of the miniature x-ray source made in accordance with the invention, prior to evacuation of the source.

FIG. 2 is a cross-section of an embodiment similar to FIG. 1, but using a different cathode construction.

FIG. 3 is a cross-section of another embodiment similar to FIG. 1, but with a different feedthru.

FIG. 4 illustrates in cross-section an embodiment similar to FIG. 3, but with a different feedthru.

FIG. 5 illustrates the embodiment of FIG. 4 with the vacuum tube crimped off.

FIG. 6 illustrates in cross-section an embodiment of the high voltage connection to the anode.

DETAILED DESCRIPTION OF THE INVENTION

Figure 7:
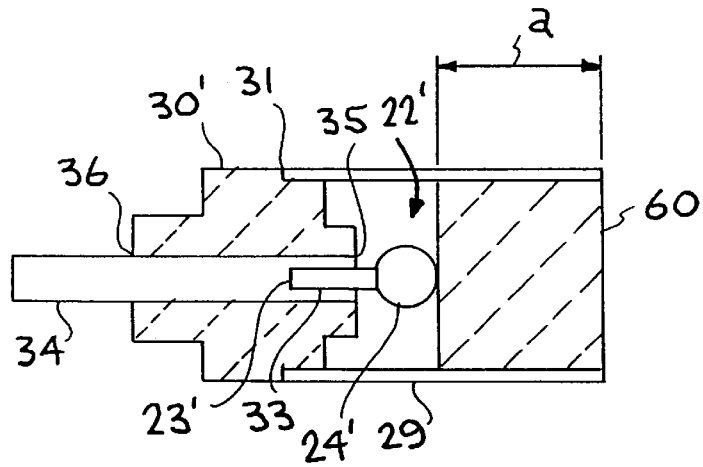
FIGS. 7 and 8 illustrate the brazes and technique for brazing components of the miniature x-ray source.

The present invention is directed to a miniature x-ray source. The x-ray source is of millimeter scale size and is capable of producing broad spectrum x-ray emission over a wide range of x-ray energies (1 to 30). The compact size and potential for remote operation allows the x-ray source to be placed, for example, adjacent to a material sample undergoing x-ray analysis. This improves the signal levels and allows for local measurements in confined or remote locations. In addition, some medical treatments require compact x-ray sources that can be placed in proximity to the region to be treated, such as arterial disease, cancer, restenosis, and tumors.

The miniature x-ray source basically consists of the following components: an anode made from a tungsten ball, or other curved configuration, on the end of a tungsten shaft; a cathode, either of a cold filament type (field emission) or of a hot filament type; a high voltage feedthru made, for example, of an insulator material, such as alumina, sapphire, and diamond; a highly x-ray transparent vacuum housing made, for example, of PBN, sapphire, alumina, glass, diamond, or other insulating materials; a high voltage connection to a high voltage cable, such as a coaxial cable, a pump-through member or cathode mount with vacuum pump-out channels or ports, and a vacuum tube for crimp-off containing a getter.

Referring now to the drawings, FIGS. 1–4 illustrate embodiments of the miniature x-ray source, with FIG. 5 illustrating a crimp-off of the tube of FIG. 4, and FIG. 6 illustrating the high voltage connection to the anode. The FIG. 1 embodiment comprises a vacuum tube 10, constructed of tantalum, copper, stainless steel or other metal, and adapted to be connected at one end 11 to a vacuum system, indicated generally at 12, and at an opposite end 13 to a cathode retainer or pump-through member 14, constructed of tantalum, copper, stainless steel or other metal by, for example, a laser fusion weld 15. The pump-through member of the invention provides support for the cathode and also provides openings through which the interior space of the x-ray source is pumped to vacuum. The cathode retainer or pump-through ring 14 includes plurality radial channels or openings 16 and a central opening 17, in which a cathode 18 is mounted. A compact vacuum tube assembly includes a vacuum tube 10, cathode 18, and pump-through member 14, and is used to pump out the system. Cathode 18, for example, may be a diamond coated tungsten or graphite emitter. A highly x-ray transparent vacuum housing 19, composed of transparent material such as PBN, is secured to retainer or pump- through member 14, as by an Incusil braze 20, for example, and includes an elongated end section constituting a feedthru 21 in which an anode, generally indicated at 22, is mounted. The vacuum tube 10, vacuum housing 19, and pump-through member 14 form an assembly of the x-ray source. Anode 22, in this embodiment, comprises a tungsten shaft 23 and a tungsten ball 24; but can be Kovar, tantalum, or other mid to high z-metal to obtain good x-ray yield. While not shown, a feedthru made of Maycor may be located in the PBN feedthru 21. The tungsten shaft 23 may be secured to the feedthru 21 by either an Incusil or Cusil braze indicated at 25. A getter 26, such as Zr, V, Fe, Ti or ST707 made by SAES getters is secured to cathode 18.

The FIG. 2 embodiment is generally similar to FIG. 1 except that the pump-through member and getter are combined, and similar components will be given corresponding reference numerals. The cathode retainer or pump-through in this embodiment comprises a getter pump-through ring or member 27, within which the cathode 18 is secured, and is secured to the tube 10 which, in this embodiment, is copper, and to PBN vacuum housing 19 by an Incusil braze 28.

FIG. 3 differs from the FIG. 1 embodiment in the composition of the anode feedthru and vacuum housing, and similar components are given corresponding reference numerals. In FIG. 3, the vacuum housing comprises a PBN tube 29 secured at one end to pump-through member 14 by an Incusil braze 20 and at an opposite end to a feedthru 30 by an Incusil braze 31, the feedthru 30 being constructed of Maycor or a ceramic, such as alumina, made by Inta, and anode 22 is secured in feedthru 30 by a Cusil braze 32. By way of example, the length of PBN tube 29, as indicated by arrow a is 0.2500 inch, with cathode 18 and ball 24 of anode 22 spaced to define a gap indicated by arrow b as 0.043 inch, with the distance from the tip of cathode 18 to the end of tube 29 being 0.0570 inch, as indicated by arrow c, and with the distance from the end of ball 24 to the end of tube 29 being 0.150 inch, as indicated by arrow d.

FIG. 4 differs from FIG. 3 in the construction of the feedthru and the anode, and similar components will be given corresponding reference numerals. In FIG. 4, the anode, generally indicated at 22', comprises a shaft 23' and a ball 24', with the shaft 23' being secured in an opening 33 of a pin 34, made, for example, of Kovar, supplied by Goodfellow. The shaft 23' is secured in opening 33 by a Cusil braze 35, with the pin 34 secured in feedthru 30' by a silver braze 36 and adapted to be connected to a high voltage cable, as shown in FIG. 6. The distances indicated by arrows a, b, c, and d are the same as in the FIG. 3 embodiment. In FIG. 4, the end 11 of tube 10 is provided with a flange 37 having a diameter of 1.33 inch for securing the tube 10 to the vacuum system 12 of FIG. 1.

FIG. 5 illustrates the FIG. 4 embodiment after vacuum has been pulled and tube 10 crimped-off, as indicated at 38, whereby the area within tube 10 and vacuum housing 29 defines a vacuum chamber 39. Following the brazing operations and crimp-off of tube 10, the PBN vacuum housing 29 is then coated with a thin layer 40 of aluminum (~5000 Å) to provide a path for the return current. The thin aluminum has a high degree of x-ray transmission.

The anode 22 of FIGS. 1–5 may be made from a high atomic number metal, such as tungsten, tantalum, gold, or a gold coating over another conducting material. The high atomic number metal produces x-rays with high efficiency under electron bombardment. The end 24 shape is spherical with a typical diameter of 1.3 mm. A known technique for producing the spherical anodes is used, and the spherical anodes used currently are fabricated by heating a 0.5 mm diameter rod of material in an electric arc and then rapidly removing the electric power. The rapid cooling and surface tension produce a smooth sphere on the tip of the rod. The diameter of the sphere can be controlled by adjusting the electrical power or its duration. The surface of the sphere has a high degree of smoothness to minimize electrical arcing when high voltage is applied. Nonspherical anode shapes can be and have been used. A cylindrical geometry rod with a rounded tip has been successfully operated. This allows the design of the anode assembly to be altered to achieve a given desired operational regime. The geometry used needs to have rounded edges and smooth surfaces to minimize high electric fields and electric arcing.

Two types of field emission cathodes, such as illustrated at 18 in FIGS. 1–5, have been used. One is fabricated from graphite by precision machining. The other is made from tungsten and coated with CVD diamond. Both types of cathodes emit electrons by field emission when a sufficiently high electric field is applied between the tip of the cathode and the anode. A field of 15 kV over 1 mm is typically used to produce a current of about 100 microamps through the field emission process. The geometry of both types of cathodes consists of a 0.5 mm diameter rod with a 60-degree full angle cone at the end. The tip of the cone typically has a 10–30 micron radius of curvature. Varying the cone angle alters the trajectory of the electrons emitted from the cathode. The ~60-degree cone angle and ~1 mm gap between the cathode and the anode produces a fairly uniform electron distribution impacting on the anode tip.

The anode 22 is connected to positive high voltage and the cathode 18 is connected to ground. The exterior of at least the vacuum housing 29 is coated with a thin conducting layer 40, such as 5000 Å of aluminum, as shown in FIG. 5, and electrically grounded. This electrical configuration results in favorable electron trajectories with the emitted electrons impacting on the anode as desired for optimal x-ray production. Reverse biasing is possible and will produce the same current for a given voltage, but some of the emitted electrons will impact on the inner wall of the assembly rather than on the anode. This can result in an increased tendency to produce surface arcing on the insulating wall and will also result in reduced x-ray yield.

The anode-cathode gap, illustrated at b in FIG. 5, of 1 mm is optimum for producing a current of ~100 microamps at a voltage of 15 kV with a 3 mm diameter assembly. Increasing the gap reduces the current for a given voltage, while decreasing the gap size increases the current for a given voltage. Achieving the same current for a given voltage requires the use of a smaller gap as the diameter of the assembly is reduced. This potential for varying component dimensions allows the design of the assembly to be altered to achieve a given desired operational regime for a given size.

The vacuum housing, indicated at 29 in FIG. 5, consists of PBN of commercial manufacture. The PBN is highly transparent to the x-rays produced, sufficiently strong to withstand the mechanical forces produced by both normal handling and the atmospheric forces pushing in on the evacuated assembly, and has a high electrical resistivity to minimize the potential for surface arcing and electrical breakdown. The PBN vacuum housing is the insulating space between the anode and the cathode. For the small dimensions of the miniature x-ray source the high electrical breakdown characteristics of the PBN is crucial. The layered structure of the PBN lends itself to vacuum brazing. Electron microscope imagery of PBN joints show a wicking up into the layers of the braze material. This creates a strong vacuum tight bond necessary for the assembly of the miniature x-ray system. The PBN has a degree of porosity associated with it. This porosity can create virtual leaks with the assembly that can reduce or ruin the vacuum. These virtual leaks can be overcome by heating and pumping on the assembly prior to crimp-off for extended periods of time (days), or by coating the inside of the PBN with thin layers of aluminum oxide, amorphous boron nitride, glass, or other insulating material. The vacuum housing 29 could also be manufactured from other materials such as alumina, glass, beryllium, oxide, or other insulating materials.

The cathode 18 is mounted on a pump-through ring or member 14, composed of tantalum, with pump-through ring or member 14 having channels 16 therein, as shown in FIG. 5, to provide for vacuum pump-out of the complete assembly. The attachment of the cathode to the ring can be achieved with a vacuum braze, laser weld, mechanical crimp, or any other method which provides for electrical continuity between the cathode and the ring. The pump-through ring 14 can be made of any conducting material with sufficient mechanical strength to be a structural component of the assembly and with a close match in thermal expansion coefficient such that cracking of the assembly during the brazing process does not occur. Tantalum and PBN have compatible coefficients of thermal expansion. The tantalum pump-through ring is vacuum brazed to the boron nitride vacuum housing and laser welded to the tantalum or copper vacuum tube 10 for containing the getter 26 and for vacuum pump out.

The vacuum or crimp-off tube 10 is made of tantalum or copper and is used for the vacuum pump down of the assembly and as a location for placing the getter material 26 to maintain the vacuum after crimp-off, as shown in FIG. 5. The crimp-off tube 10 can be made of any material that can be crimped to produce a vacuum tight seal. The crimp-off is achieved using a crimp-off tool that maintains tube diameter at the crimp joint. The crimp is made once the vacuum in the assembly forming chamber 39 is sufficiently low for electrical operation (better than 10-6 Torr), and, once extended, bake-out and operation at maximum desired voltage has been conducted to minimize outgassing of the assembly components. Means for evacuating the assembly and maintaining a vacuum in the assembly may include the vacuum tube for crimping off, the vacuum system used to evacuate the interior of the x-ray source, the getter, and the pump-through member.

In accordance with methods known in the art for manufacture of miniature x-ray tubes, such as in PCT Publication WO 97/07740, the crimp-off tube and process could be eliminated and the x-ray tube sealed with a vacuum brazing process after an extended bake-out at high vacuum. Then a metal endcap would be used to hold the getter material in place. Alternatively, the getter 26 can be manufactured in the shape of a donut and mounted at the base of the cathode, as shown at 27 in FIG. 2. This location is essentially electric field free and therefore the getter would present no internal electrical problems associated with surface arcing or breakdown.

The getter 26 may be SAES ST 707, manufactured by SAES. This is a material that activates after baking under vacuum at 300° C. for two hours. Any comparable getter could be used as long as the getter does not require any power or processing after activation.

The high voltage feedthru, shown at 19 in FIGS. 1 and 2 and at 30 and 30' in FIGS. 3–5, consists, for example, of an alumina (ceramics) or PBN component with a cylindrical channel to allow for the anode rod 23 or Kovar pin 34 containing rod 23' to pass through to the exterior. The feedthru could be made from Maycor or other electrically insulated materials. The anode rod is brazed in place to achieve a vacuum seal. A portion of the feedthru extends over the anode rod on the exterior to increase the path length from the rod to the outer diameter of the assembly. This minimizes the potential for arcing in high voltage connection. The high voltage feedthru could be eliminated by adding this extension for the anode rod to the PBN vacuum housing 29, as shown in FIGS. 1 and 2. This would simplify the assembly and eliminate one braze joint.

The high voltage feedthru, the PBN vacuum housing, the cathode pump through ring, and crimp-off tube are joined together using brazing or welding techniques, as illustrated in FIGS. 1–5. The PBN vacuum housing is then coated with, for example, a thin layer 40 of aluminum (~5000 Å) to provide a path for the return current, and, as pointed out above, the layer 40 of thin aluminum having a high degree of x-ray transmission.

The high voltage connection to the anode consists of the attachment of a commercially available coaxial cable using Teflon or silicone insulation. The exterior insulation and coaxial conductor are stripped back and the center conductor is soldered to the anode rod. The solder may therefore serve as the high voltage connection for attaching the high voltage cable. Silicon or Teflon is then injection-molded around the solder joint and the exterior conductor is then slid into place over the now-insulated connection. A brass or other conducting metal shell is then placed over the outer conductor and the shell is attached by soldering, crimping, or conductive glue to the aluminum coating on the PBN housing completing the electrical circuit. A thin plastic coating can be deposited over the entire assembly to provide for chemical protection. The grounded exterior conductor provides electrical protection.

FIG. 6 illustrates an embodiment of the high voltage connection to an anode 42', which includes a rod 43 and a ball or sphere 44, and with ball 44 located within PBN vacuum housing 45 having a central opening 46 and a cut-away end section 47. Anode rod 43 extends through opening 46 into cutaway end section 47, and is secured therein by a Cusil braze 48, for example. A coaxial cable, generally indicated at 49, includes a pair of coaxial conductors 50 and 51, composed of a plurality of wires, and enclosed within a Teflon or silicone insulator layer 52. The exterior insulation layer 52 and outer coaxial conductor 51 are stripped back, with insulation layer 52 being stripped further back than conductor 51, and the inner or center conductor 50 is soldered to anode rod 43, as indicated at 53. Silicon or Teflon is then injection-molded around the solder joint 53 and the exterior of center conductor 50, as indicated at 54. A brass or other conducting metal shell 55 is placed over the exposed end of outer conductor 51 and the end of vacuum housing 45 containing the cut-away end section 47 and attached by soldering, crimping, or conductive glue to the conductor 51 and to the aluminum coating or layer 40 on the PBN housing completing the electrical circuit. A thin plastic coating 56 can be deposited over the entire assembly to provide chemical protection. The grounded exterior conductor 51 provides electrical protection. By way of example, the length of PBN vacuum housing 45, as indicated by arrow a is 0.329±0.005 inch, with the distance from the end of housing 45 to the center of ball 44, as indicated by arrow b, is 0.209±0.005 inch, and the length of the cut-away section 47 of housing 45, as indicated by arrow c, is 0.116±0.005 inch.

Figure 8:
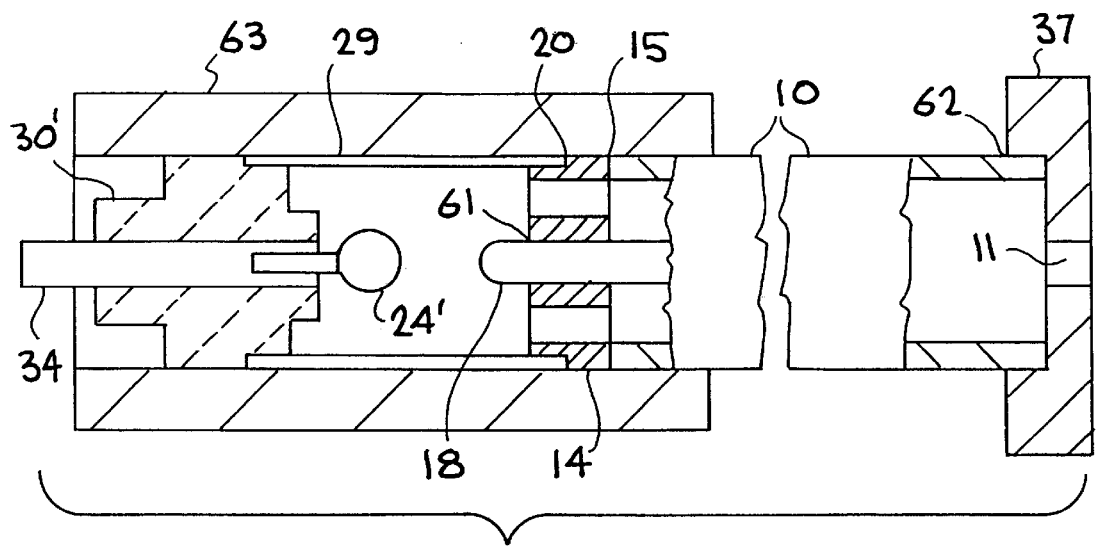

FIGS. 7 and 8 illustrate the braze procedure for the FIGS. 4–5 embodiment. As seen in FIG. 7, the PBN vacuum housing 29 is positioned around an alumina spacer 60 having a height indicated by arrows of 0.103 inch, which provides support for tungsten anode 22' having rod 23' in abutment with a Kovar pen 34, which extends through a ceramic high voltage feedthru 30', with anode rod 23' being secured to Kovar pin 34 by a Cusil braze 35, and Kovar pin 34 being secured in feedthru 30' by a silver braze 36, and feedthru 30' being secured to PBN housing 29 by a Cusil braze 31. The assembly of FIG. 7 is then secured to the pump-through ring 14 having cathode 18 secured therein by a solder or other means indicated at 61, the pump-through ring 14 having been secured to the tantalum vacuum or crimp-off tube 10 by laser fusion weld 15, and tube 10 is secured at end 11 to a flange 37 via a weld or braze 62. The tube 10 is secured to flange 37 by weld or braze 62 and PBN housing 29 is positioned on pump-through ring 14 and retained thereon during brazing by a weight 63 composed of 2 grams of stainless steel, whereafter an Incusil braze 20 secures housing 29 to pump-through ring 14.

The braze procedure is as follows: The components are cleaned with acetone and a foil of Incusil-15 ABA braze material is placed between the surfaces of the components to be brazed together. These are placed in a vacuum chamber and the chamber is evacuated with a vacuum pump to a pressure of 10E-6 Torr in about 30 minutes. The components are then heated under vacuum for 20 minutes to a temperature of 600° C. using a radiation heater. They are held at this temperature for 3 minutes before being heated over a 5-minute period to 750° C. The components are then held at 750° C. for 5 minutes and then allowed to cool for more than one hour in the vacuum chamber. The brazed components are then removed from the vacuum chamber for use. Lower temperature brazing of some components has been achieved with the use of Cusil ABA braze material.

Operation of the system is achieved by slowly increasing the voltage applied to the anode-cathode gap while the current is monitored. A practical operational regime has been found using a current and voltage stabilized power supply. In this mode the voltage is raised to the level required to produce a given x-ray spectrum. The gap has been previously set to produce the desired current and hence desired amount of x-rays. The current regulation is then set to not exceed this current level. The voltage limit setting on the power supply is then increased approximately 10 percent. If the current starts to drop due to irreproducibilities in the field emission, then the power supply allows an increase in voltage which increases the current back to the desired level. If the field emission variations increase the current, then the current regulation of the power supply reduces the voltage, which reduces the current. Since, for field emission cathodes, the current varies exponentially with the voltage, small variations in voltage, which have minimal effect on the x-ray spectrum, can be used to stabilize the field emission process.

It has thus been shown that the present invention provides an x-ray source which is capable of producing broad spectrum x-ray emission over a wide range of x-ray energies (5–40 keV or higher) using high voltages (5–40 kV or higher). The miniature x-ray source has a wide range of applications in the field of medical treatment and in the field of material analysis. The x-ray source can be inserted into extremely confined spaces, and can be located in close proximity to a point of use.

While particular embodiments, materials, parameters, etc., have been described and/or illustrated to exemplify and teach the principles of the invention, such are not intended to be limiting. Modifications and changes may become apparent to those skilled in the art, and it is intended that the invention should be limited only by the scope of the appended claims.

What is claimed is:

1. A miniature x-ray source capable of producing broad spectrum x-ray emission over a wide range of x-ray energies, comprising:

an assembly, including a vacuum housing and a vacuum tube, both the vacuum housing and the vacuum tube being connected to a vacuum pump-through member, said vacuum pump-through member defining openings therethrough:

an anode mounted in said vacuum housing of said assembly;

a cathode mounted in said vacuum pump-through member of said assembly in spaced relation to said anode;

said assembly including a high voltage feedthru operatively connected to said anode;

a high voltage connection for attaching a high voltage cable to said anode through said high voltage feedthru; and means operatively connected to said assembly for evacuating said assembly and maintaining a vacuum in said assembly.

2. The x-ray source of claim 1, wherein said anode includes an end section and a rod section, said end section having at least rounded edges and smooth surfaces to minimize high electric fields and electrical arcing.

3. The x-ray source of claim 1, wherein said end section of said anode includes a spherical end surface.

4. The x-ray source of claim 1, wherein said vacuum housing of said assembly is composed of pyrolytic boron nitride.

5. The x-ray source of claim 4, wherein said high voltage feedthru comprises a reduced diameter end section of said vacuum housing of said assembly.

6. The x-ray source of claim 5, wherein said anode comprises a rod section and a spherical end section, said rod section being secured in said reduced diameter end section of said vacuum housing of said assembly.

7. The x-ray source of claim 4, wherein said high voltage feedthru is secured in an end section of said vacuum housing of said assembly.

8. The x-ray source of claim 7, wherein said anode is secured in said high voltage feedthru.

9. The x-ray source of claim 8, further comprising a pin mounted in said member and said anode being connected to said pin.

10. The x-ray source of claim 1, wherein said means includes said vacuum pump-through member, said vacuum tube adapted to be connected to a vacuum system, and a getter material located in said vacuum tube, whereby a vacuum is drawn to evacuate said assembly, and whereafter said vacuum tube is crimped-off to form a vacuum chamber.

11. The x-ray source of claim 10, wherein said getter material is secured to said vacuum pump-through member.

12. The x-ray source of claim 10, wherein said getter material is incorporated into said vacuum pump-through member.

13. The x-ray source of claim 1, wherein said vacuum housing is composed of pyrolytic boron nitride and said vacuum tube is composed of a metal, said vacuum housing including said high voltage feedthru, said anode being secured in said high voltage feedthru.

14. The x-ray source of claim 13, further comprising a pin extending through said high-voltage feedthru and secured to said anode, said high voltage connection being secured to said pin.

15. The x-ray source of claim 1, wherein said assembly has an exterior diameter of about 4 mm, wherein said anode and said cathode are mounted to define a gap there between of about 1 mm, and wherein said high voltage connection provides a voltage in the range of about 5–40 kV, whereby x-rays having an energy of about 5–40 keV are produced.

16. An x-ray source comprising:
a compact vacuum tube assembly including a pump-through member for initial vacuum pump down and crimp-off, said pump-through member containing a cathode, and said pump-through member having openings therethrough;
an anode within said assembly;
a high voltage feedthru connected to said anode for delivering high voltage to said anode; and
a high voltage connection for attaching a compact high voltage cable to said high voltage feedthru connected to said high voltage feedthru.

17. The x-ray source of claim 16, further comprising a getter for maintaining high vacuum.

18. The x-ray source of claim 16, where the pump-through member for initial vacuum pump down comprises a getter for maintaining a high vacuum.

19. A miniature x-ray source capable of producing broad spectrum x-ray emission over a wide range of x-ray energies, comprising:
an assembly,
an anode mounted in said assembly,
a cathode mounted in said assembly in spaced relation to said anode,
said assembly including a high voltage feedthru operatively connected to said anode,
a high voltage connection for attaching a high voltage cable to said anode through said high voltage feedthru, and
means for evacuating said assembly, including a vacuum pump-through member operatively connected to said housing assembly, and means including a getter material for maintaining a vacuum in said assembly.

20. The x-ray source of claim 19, wherein said assembly includes a section highly transparent to x-rays and selected from a group of materials consisting of pyrolytic boron nitride, sapphire, diamond, alumina and glass.

21. The x-ray source of claim 19, wherein said assembly includes a first section in which said anode is mounted and a second section in which said cathode is mounted, said first and second sections being interconnected via said vacuum pump through member.

22. The x-ray source of claim 21, wherein said cathode is mounted in said vacuum pump through member.

23. The x-ray source of claim 21, wherein said first section of said assembly is composed of pyrolytic boron nitride.

24. The x-ray source of claim 19, wherein said means includes a tube forming a part of said assembly and which is secured to said vacuum pump through member and adapted to be connected to a vacuum system, and a getter material located in said tube, whereby a vacuum is drawn to evacuate said assembly, and whereafter said tube is crimped-off to form a vacuum chamber within said assembly.

25. The x-ray source of claim 24, wherein said getter material is secured to said vacuum pump through member.

26. The x-ray source of claim 24, wherein said getter material is incorporated into said vacuum pump through member.

27. The x-ray source of claim 19, wherein said assembly comprises a first section composed of pyrolytic boron nitride and a second section composed of a metal, said sections being secured to opposite sides of said vacuum pump through member in which said cathode is mounted, said first section of said assembly having a high voltage feedthru secured, said anode being secured thereto in said high voltage feedthru.

28. The x-ray source of claim 27, additionally including a pin extending through said high-voltage feedthru and secured to said anode, said high voltage connection being secured to said pin.

* * * * *

UNITED STATES PATENT AND TRADEMARK OFFICE
CERTIFICATE OF CORRECTION

PATENT NO.   : 6,353,658 B1  
DATED        : March 5, 2002  
INVENTOR(S)  : James E. Trebes et al.

It is certified that error appears in the above-identified patent and that said Letters Patent is hereby corrected as shown below:

<u>Title page,</u>  
Item [73], add the following: -- XRT Corp. St. Paul, Minnesota --

Signed and Sealed this

Ninth Day of July, 2002

*Attest:*

*Attesting Officer*

JAMES E. ROGAN  
*Director of the United States Patent and Trademark Office*